United States Patent
Wigstrom et al.

(10) Patent No.: US 7,656,990 B2
(45) Date of Patent: Feb. 2, 2010

(54) ADAPTIVE ANISOTROPIC FILTERING OF PROJECTION DATA FOR COMPUTED TOMOGRAPHY

(75) Inventors: Lars Wigstrom, Palo Alto, CA (US); Rebecca Fahrig, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 303 days.

(21) Appl. No.: 11/533,289

(22) Filed: Sep. 19, 2006

(65) Prior Publication Data

US 2008/0069294 A1    Mar. 20, 2008

(51) Int. Cl.
*A61B 6/00* (2006.01)
(52) U.S. Cl. ......................................................... 378/4
(58) Field of Classification Search ....................... 378/4
See application file for complete search history.

(56) References Cited

U.S. PATENT DOCUMENTS

| | | | | |
|---|---|---|---|---|
| 3,993,976 | A * | 11/1976 | Ginsburg | 382/211 |
| 4,729,100 | A * | 3/1988 | Tsujii | 378/4 |
| 4,903,204 | A * | 2/1990 | Dobbins, III | 382/255 |
| 5,003,618 | A * | 3/1991 | Meno | 382/261 |
| 5,091,925 | A * | 2/1992 | Haendle et al. | 378/98.2 |
| 5,416,815 | A * | 5/1995 | Hsieh | 378/4 |
| 5,558,091 | A * | 9/1996 | Acker et al. | 600/424 |
| 5,671,263 | A * | 9/1997 | Ching-Ming | 378/8 |
| 5,957,844 | A * | 9/1999 | Dekel et al. | 600/439 |
| 6,094,467 | A * | 7/2000 | Gayer et al. | 378/4 |
| 6,196,715 | B1 * | 3/2001 | Nambu et al. | 378/197 |
| 6,215,841 | B1 * | 4/2001 | Hsieh | 378/8 |
| 6,591,004 | B1 * | 7/2003 | VanEssen et al. | 382/154 |
| 6,898,263 | B2 * | 5/2005 | Avinash et al. | 378/4 |
| 2002/0071600 | A1 * | 6/2002 | Yamada | 382/132 |
| 2003/0076988 | A1 * | 4/2003 | Liang et al. | 382/131 |
| 2005/0286749 | A1 * | 12/2005 | De Man et al. | 382/131 |

(Continued)

FOREIGN PATENT DOCUMENTS

WO    2005091219 A1    9/2005

OTHER PUBLICATIONS

Hsieh, Jiang, "Adaptive Streak Artifact Reduction in Computed Tomography Resulting from Excessive X-ray Photon Noise", Med. Phys. 25 (11), Nov. 1998, pp. 2139-2147.

(Continued)

*Primary Examiner*—Edward J Glick
*Assistant Examiner*—Alexander H Taningco
(74) *Attorney, Agent, or Firm*—Beyer Law Group LLP

(57) ABSTRACT

CT imaging is enhanced by adaptively filtering x-ray attenuation data prior to image reconstruction. Detected x-ray projection data are adaptively and anisotropically filtered based on the locally estimated orientation of structures within the projection data from an object being imaged at a plurality of rotation positions. The detected x-ray data are uniformly low pass filtered to preserve the local mean values in the data, while the high pass filtering is controlled based on the estimated orientations. The resulting filtered data provide projection data with smoothing along the structures while maintaining sharpness along edges. Image noise and noise induced streak artifacts are reduced without increased blurring along edges in the reconstructed images. The enhanced image allows reduced x-ray dose while maintaining image quality.

14 Claims, 4 Drawing Sheets

U.S. PATENT DOCUMENTS

2006/0045371 A1  3/2006  Li
2006/0062485 A1  3/2006  Li
2006/0072844 A1* 4/2006  Wang et al. ............... 382/254

OTHER PUBLICATIONS

Kahelrieβet al., "Generalized Multi-dimensional Adaptive Filtering for Conventional and Sprial Single-Slice, Multi-Slice, and Cone Beam CT", Med. Phys. 28 (4), Apr. 2001, pp. 475-490.

La Riviere et al., "Reduction of Noise-Induced Streak Artifacts in X-Ray Computer Tomography Through Spline-Based Penalized-Likelihood Sinogram Smoothing", IEEE Transaction on Medical Imaging, vol. 24, No. 1, Jan. 2005, pp. 105-111.

Lu et al., "Adaptive Noise Reduction Toward Low-Dose Computer Tomography", Medical Imaging 2003: Physics of Medical Imaging, M. J. Yaffe, L. E. Antonuk, Editors, Proceedings of SPIE vol. 5030 (2003).

Wang et al., "Noise Reduction for Low-Dose Helical CT by Fully 3D Penalized Weighted Least-Squares Sinogram Smoothing", Proc. SPIE vol. 6142, 61424E, Medical Imaging 2006: Physics of Medical Imaging; Michael J. Flynn, Jiang Hsieh; Eds.

Westin et al., "Affine Adaptive Filtering of CT Data", Medical Imaging Analysis 4 (2000) 161-177.

Westin et al., "Three-Dimensional Adaptive Filtering in Magnetic Resonance Angiography", Journal of Magnetic Resonance Imaging 14:63-71 (2001).

* cited by examiner

Original

Filtered

ADAPTIVE ANISOTROPIC FILTERING OF PROJECTION DATA FOR COMPUTED TOMOGRAPHY

GOVERNMENT RIGHTS

The U.S. Government has rights in the disclosed invention pursuant to NIH Grant No. 003524 to Stanford University.

BACKGROUND OF THE INVENTION

This invention relates generally to computed tomography (CT) and more particularly the invention relates to processing of CT image data to reduce adverse noise effects in data acquired using a low x-ray dose.

Cross-sectional images of a patient using x-ray computed tomography have long been employed in medical practice. Briefly, computed tomography is the reconstruction by computer of a tomographic slice or a three-dimensional (3D) image volume of an object or patient. It is generated from multiple x-ray absorption measurements in a scan made around the object's periphery. These projections can be obtained using, for example, a conventional CT scanner with an x-ray source and a detector rotating at a relatively high speed, or with a source and a detector mounted on a C-arm that rotates more slowly around the patient. The fidelity of the image depends upon the nature of the x-ray source and the detectors, the number and speed of the measurements made, and details of the reconstruction algorithm.

An x-ray detector detects a beam of x-rays passing through the body which are attenuated by absorption and by scattering. The amount of absorption depends on the physical density, the atomic composition and the photon energy spectrum of the x-ray beam. For equivalent x-ray energy, a more dense material will attenuate the beam more than a less dense material. X-ray detectors with multiple rows of detector elements, or even a full two-dimensional (2D) matrix, will generate a 2D projection image at every rotation angle. Based on these obtained projections, a reconstruction algorithm computes an attenuation coefficient for each volume element or voxel in the slice.

With the acquisition of an increasing number of projections, it is essential to minimize the radiation dose used. Adaptive anisotropic filtering has the ability to reduce the noise level in low dose data without introducing noticeable blurring.

Three dimensional adaptive filtering as applied to magnetic resonance angiography subsequent to image reconstruction is described by Westin et al. in Journal of Magnetic Resonance Imaging 14: 63-7231 (2001). As described by Westin et al., multi-dimensional adaptive filtering is used as a technique for enhancement of images, image volumes, and volume sequences having temporal resolution. The multi-dimensional adaptive filtering method employs local orientation of structures within the image, such as lines, edges, and planes, to control a set of anisotropic filters. The method is divided into three main steps. The first step includes an estimation of the local orientation of every neighborhood in the original image by assuming that the local orientation can be described locally by a combination of simple features such as lines and planes. In a second step the orientation estimate is stabilized through low pass filtering. Finally, the orientation information is used to control the filtering of the original data in an adaptive fashion.

Li et al. U.S. Patent Publication No. US2006/0062485A1 and Spies et al. International Publication No. WO2005/091219A1 describe the use of filtering to enhance CT images including the use of processing subsequent to image reconstruction to reduce noise effects. However, post processing approaches will be less efficient in reducing for example noise induced streak artifacts compared to processing prior to image reconstruction. It is known to filter CT image data prior to image reconstruction, but it is not believed that adaptive anisotropic filtering utilizing filters that change their shape according to the input data, have been employed.

SUMMARY OF THE INVENTION

In accordance with the invention, anisotropic filtering of a stack of projection data is performed prior to image reconstruction. In a computed tomography application, a 3D stack of projection data includes multiple 2D projections acquired at different angles of rotation. The orientation of structures within the 3D space is estimated using a set of differently oriented filters, for example. The obtained representation of the local orientation is utilized to control the anisotropic filtering of the data in order to apply low pass filtering along structures while maintaining all frequency components perpendicular to the structures. Thus, the low pass filtering will reduce the high frequency noise to a degree determined by the estimated strength and continuity of structures in projection space. The direction of low pass filtering is also locally controlled by the estimated orientation. The invention is applicable to tomosynthesis, also, where the source or detector is translated rather than rotated.

The invention allows a substantial reduction in radiation dose required for obtaining 3D CT image data. Alternatively, improved image quality can be attained at a given radiation dose. The invention can be applied to four dimensions to process a time sequence of 3D projection data.

The invention and object and features thereof will be more readily apparent from the following detailed description and appended claims when taken with the drawings.

DETAILED DESCRIPTION OF ILLUSTRATIVE EMBODIMENTS

Figure 1:
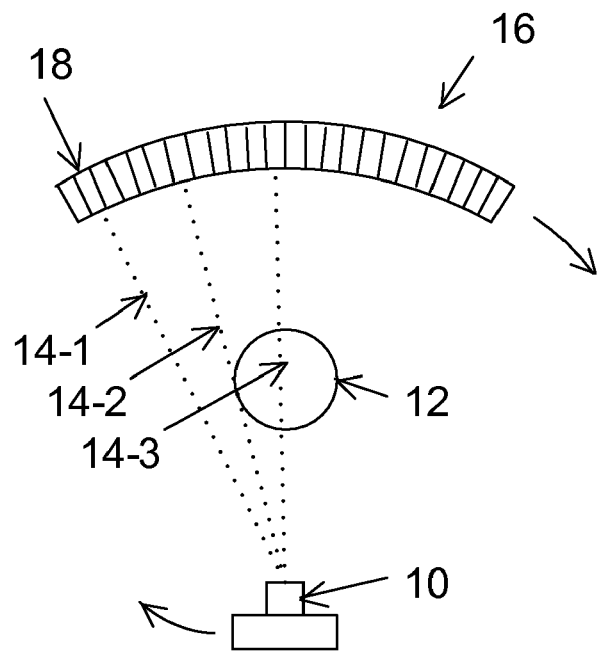
FIG. 1 is a schematic diagram of apparatus for obtaining CT data from which an image can be reconstructed.

FIG. 1 is a schematic diagram of CT apparatus including an x-ray source 10 and an x-ray detector 20 which are rotatably translated around an object 12 with detector 20 providing measurement of attenuated x-rays passing through object 12 and providing data for reconstructing an image of a slice through object 12. The x-ray source emits a fan or cone shaped beam towards a scan object such as a patient, and the beam after being attenuated by the scan object impinges upon an array of radiation detectors, which in turn produce electrical signals indicative of the attenuated beam. Multiple sources could also be used to generate a parallel x-ray beam, or a single narrow beam could be scanned across the object. The electrical signals are then transmitted to a data processing unit for analysis and image reconstruction.

As illustrated, a portion of the x-ray beam 14-1 travels directly to a detector element 22 in the array 20 without passing through object 12, a portion of the x-ray beam 14-2 passes tangentionally to object 12, and other portions of the x-ray beam 14-3 pass through object 12 and are attenuated thereby.

Figure 2:
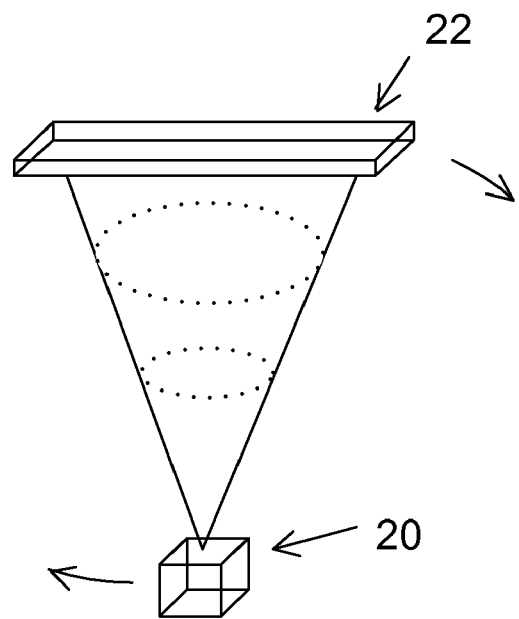
FIG. 2 shows the setup for obtaining two-dimensional projections utilizing an x-ray detector with multiple rows, or even a larger 2D detector.

With a 2D detector array 22 containing a number of parallel rows as shown in FIG. 2, attenuation measurements can be performed simultaneously for multiple fans within the cone of x-rays emitted by the source. This will reduce the number of rotations needed to acquire sufficient data for reconstruction of an image volume. With a large detector, the required projection data may even be obtained in a single rotation.

Figure 3:
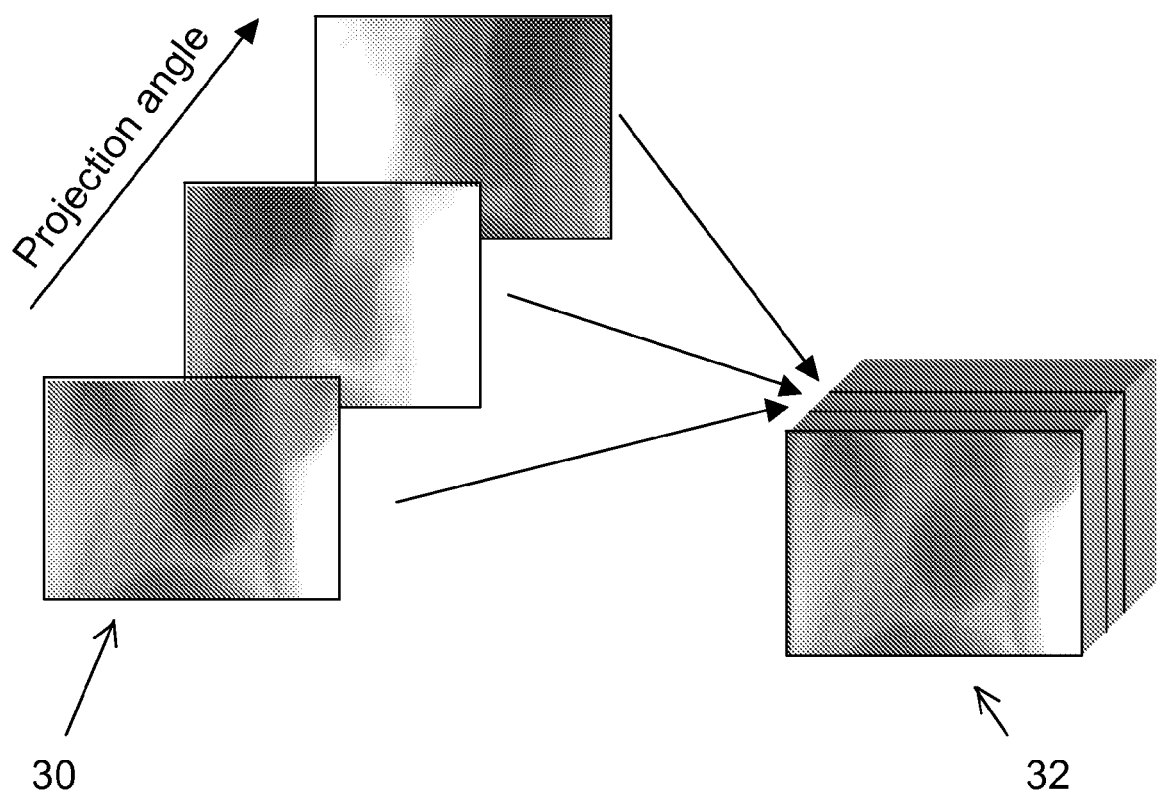
FIG. 3 illustrates how the multiple 2D projections acquired are stacked to form a 3D data set.
Figure 4:
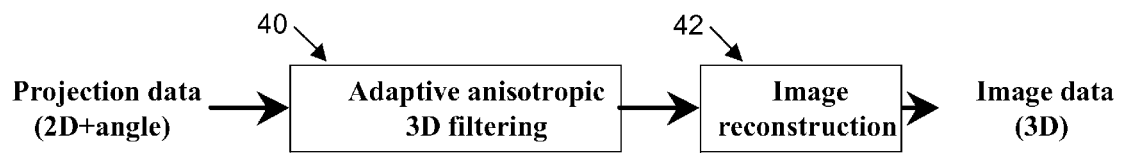
FIG. 4 is a functional block diagram of adaptive anisotropic filtering of CT data in accordance with the invention.

As shown in FIG. 3, the 2D projections 30 obtained from different angles are stacked to form a 3D data volume 32 which can be reconstructed by a reconstruction algorithm to provide images of slices through object 12 through which the x-rays traverse.

Heretofore, the adverse effects of noise in the obtained attenuation measurements have been reduced by applying anisotropic adaptive filtering of the image data after image reconstruction. Since noise in the projection data will introduce not only noise in the reconstructed images but also for example streak artifacts, attacking the problem already in the raw data domain will be more efficient. Other approaches to adaptive filtering in projection space have not used filters that locally adapt their spatial orientation to structures in the data. This will result in more blurring since not only noise but also real structures will be subject to the smoothing.

In accordance with the invention, adaptive anisotropic 3D filtering is applied to the projection data as generated by detector 20 prior to image reconstruction, as illustrated schematically in FIG. 2. Here the 3D anisotropic filtering at 40 is used to filter a stack of projection image data with the adaptive anisotropic filtering being based on the orientation of structures within the three dimensional space as estimated using a set of differently oriented filters. The attained tensor representation of the local orientation is utilized to control the anisotropic filtering of the data in order to apply low pass filtering along structures while maintaining all frequency components perpendicular to the structures. The adaptive anisotropic filtered x-ray data are then used for image reconstruction at 42 from which an image is displayed.

Figure 5:
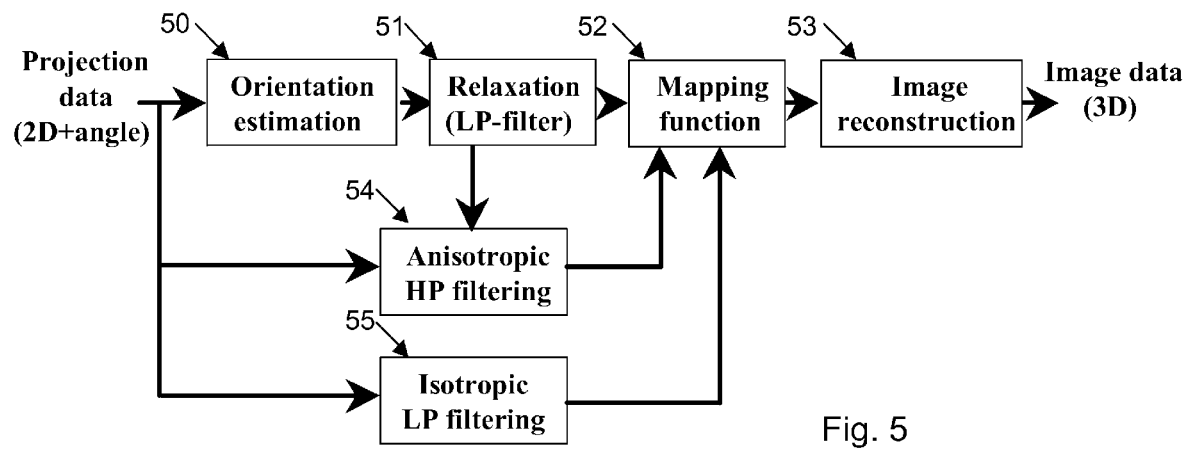
FIG. 5 is a more detailed functional block diagram of adaptive anisotropic filtering of image data prior to image reconstruction in accordance with the invention.

More particularly, as shown in FIG. 5, a description of the local structure is computed at every location within the stack of projection data at 50. This can for example be performed using a set of differently oriented filters, with each filter being sensitive to structures in a particular direction in 3D space. The response from these individual filters can be combined using a representation, for example a tensor, which can describe both the orientation and magnitude of these structures. The obtained representation of the local orientation may be subject to a relaxation or low pass filtering 51 and the result subsequently used to control the anisotropic high pass filtering at 54. This filtering step can for example be performed using the output from a number of differently oriented high pass filters combined according to the orientation estimate so that high frequency components are preserved across detected structures but not parallel to these. In this example, an isotropic low pass filtering 55 is performed in order to always maintain the low frequency components in the input signal. The filtered x-ray projection data are then recombined at mapping function 52, which uses the orientation estimate to determine how much of the anisotropic high frequency content that will be preserved. Where no apparent structure is found, high frequency content is reduced. Image reconstruction of the filtered data using for example the known Feldkamp reconstruction algorithm occurs at 53.

The low pass isotropic filtering is always the same in order to preserve the local mean value (DC component) in the projection data, while the high pass filter component is adaptively controlled to reduce the noise level in the low dose data without introducing noticeable blurring. When there is no apparent structure, the high pass filtering is reduced accordingly, which is equivalent to smoothing the data, When performing this filtering prior to image reconstruction, noise induced artifacts can be reduced more efficiently compared to processing in the image domain.

Figure 6:
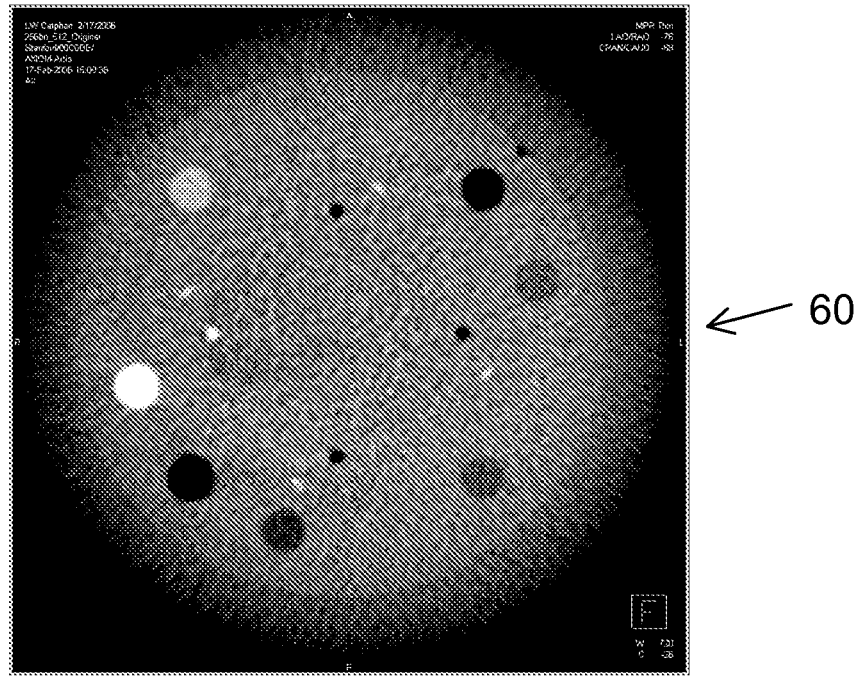
FIG. 6 illustrates reconstructed images without and with adaptively filtered data in accordance with the invention.
Figure 6:
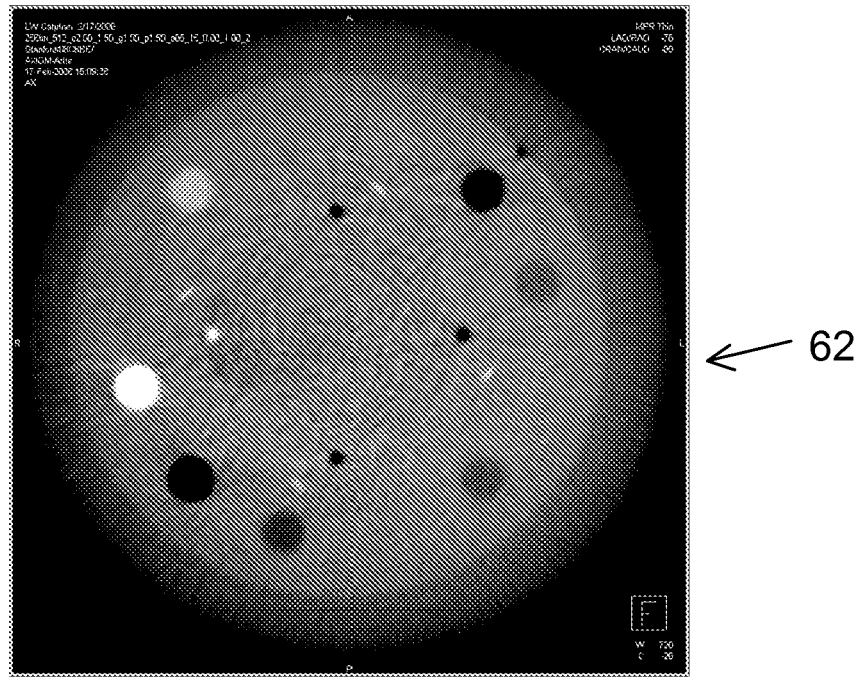

The use of adaptive anisotropic filtering in accordance with the invention can substantially reduce the radiation dose required for obtaining 3D CT image data. A reduction in the required radiation dose is important for most applications using 3D x-ray techniques. Alternatively, improved image quality can be attained at a given dose using the adaptive anisotropic filtering of the projection data. An example of reconstructed images of a test phantom is shown in FIG. 6. Using projection data acquired with a low x-ray dose, the resulting images contain a lot of noise (60). Images reconstructed based on the adaptively filtered data have a reduced noise level while important details are still preserved (62).

While the invention has been described with reference to specific embodiments, the description is illustrative of the invention and is not to be construed as limiting the invention. For example, as noted above the invention is applicable to tomosynthesis. Thus, various modifications and applications may occur to those skilled in the art without departing from the spirit and scope of the invention as defined by the appended claims.

What is claimed is:

1. A method for enhancing an image based on projection data comprising the steps of:
   a) projecting an x-ray beam through an object of interest to an x-ray detector,
   b) collecting x-ray attenuation data (projections) using an x-ray source and a detector at a plurality of positions around the object,
   c) estimating the orientation of structures within the obtained projection data, and
   d) adaptively filtering the x-ray attenuation data based on the locally estimated orientation of structures, wherein the adaptive filtering is in projection space, and
   e) reconstructing an image using the adaptively filtered x-ray attenuation data from step d).

2. The method of claim 1 wherein high frequency x-ray attenuation data are anisotropically filtered according to structures in the measured projection data.

3. The method of claim 2 wherein high frequency components are locally reduced in directions of no apparent structure.

4. The method of claim 3 wherein low frequency x-ray attenuation data are uniformly filtered to maintain a local mean value of the projection data.

5. The method of claim 2 wherein low frequency x-ray attenuation data are uniformly filtered to maintain the local mean value of the projection data.

6. The method of claim 5, wherein the step of reconstructing an image using adaptively filtered x-ray attenuation data from step d), comprises including uniformly low pass filtered x-ray data in combination with an anisotropically filtered high pass component.

7. The method of claim 5 wherein step c) includes use of a set of differently oriented filters.

8. The method of claim 1 wherein step c) includes use of a set of differently oriented filters.

9. The method of claim 1 wherein in step e) uniformly filtered low frequency x-ray attenuation data are used.

10. The method of claim 1 wherein the projection data are CT projection data.

11. The method of claim 1 wherein the projection data are tomosynthesis projection data.

12. The method of claim 1, wherein the adaptively filtering the x-ray attenuation data provides a 3D anisotropic filtering based on the estimated orientation of structures within the obtained projection data.

13. The method of claim 12, wherein the estimated local orientation is represented in the form of a tensor, which is utilized to control the 3D anisotropic filtering.

14. The method of claim 13, wherein 2D projections from different angles are stacked to form a 3D data volume.

* * * * *

UNITED STATES PATENT AND TRADEMARK OFFICE
CERTIFICATE OF CORRECTION

PATENT NO. : 7,656,990 B2  Page 1 of 1
APPLICATION NO. : 11/533289
DATED : February 2, 2010
INVENTOR(S) : Wigstrom et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,656,990 B2 | Page 1 of 1 |
| APPLICATION NO. | : 11/533289 | |
| DATED | : February 2, 2010 | |
| INVENTOR(S) | : Wigstrom et al. | |

It is certified that error appears in the above-identified patent and that said Letters Patent is hereby corrected as shown below:

Column 1:

• Please replace lines 5-8 with:

--FEDERALLY SPONSORED RESEARCH OR DEVELOPMENT
This invention was made with Government support under contract EB003524 awarded by the National Institutes of Health. The Government has certain rights in this invention.--

Signed and Sealed this
Fifth Day of April, 2011

David J. Kappos
*Director of the United States Patent and Trademark Office*